(12) United States Patent
Nacson

(10) Patent No.: US 10,591,449 B2
(45) Date of Patent: Mar. 17, 2020

(54) WEARABLE DETECTOR FOR FENTANYL AND ITS ANALOGUES

(71) Applicant: Sabatino Nacson, Thornhill (CA)

(72) Inventor: Sabatino Nacson, Thornhill (CA)

( * ) Notice: Subject to any disclaimer, the term of this patent is extended or adjusted under 35 U.S.C. 154(b) by 0 days.

(21) Appl. No.: 16/216,713

(22) Filed: Dec. 11, 2018

(65) Prior Publication Data

US 2019/0178855 A1 Jun. 13, 2019

Related U.S. Application Data

(60) Provisional application No. 62/597,367, filed on Dec. 11, 2017.

(51) Int. Cl.
*G01N 30/72* (2006.01)
*G01N 27/62* (2006.01)
*G01N 33/00* (2006.01)
*G01N 30/88* (2006.01)
*G01N 30/00* (2006.01)

(52) U.S. Cl.
CPC ....... *G01N 30/7206* (2013.01); *G01N 27/622* (2013.01); *G01N 27/626* (2013.01); *G01N 30/88* (2013.01); *G01N 33/0047* (2013.01); *G01N 33/0063* (2013.01); *G01N 2030/0095* (2013.01); *G01N 2030/884* (2013.01); *G01N 2033/0068* (2013.01)

(58) Field of Classification Search
CPC .. G01N 30/7206; G01N 30/88; G01N 27/622; G01N 27/626; G01N 2030/0095; G01N 2030/844; G01N 2033/0068; G01N 33/0047; G01N 33/0063
USPC .......................................... 250/281, 282, 288
See application file for complete search history.

(56) References Cited

U.S. PATENT DOCUMENTS

2004/0135684 A1* 7/2004 Steinthal ................ B82Y 30/00
340/522

* cited by examiner

*Primary Examiner* — Nicole M Ippolito
*Assistant Examiner* — Hanway Chang
(74) *Attorney, Agent, or Firm* — Christensen, Fonder, Dardi & Herbert PLLC; William E. Anderson

(57) ABSTRACT

A wearable device for sensing airborne narcotics. In embodiments, the wearable device may comprise an air intake; an ionization apparatus for ionization of molecules of airborne narcotics, wherein the apparatus may comprise a heated surface in fluid communication with the intake for heating molecules of airborne narcotics to ionize said molecules; at least one collector for receiving ions resulting from said ionization, and generating a signal; an apparatus for creating electrical potential to draw said ions to said at least one collector; and an alarm generator for generating an alarm if a time gap between said creation of ions and said signal indicates a presence of an airborne narcotic.

4 Claims, 2 Drawing Sheets

WEARABLE DETECTOR FOR FENTANYL AND ITS ANALOGUES

RELATED APPLICATIONS

This application claims the benefit of U.S. Provisional Application No. 62/597,367, entitled "Wearable Detector for Fentanyl and Its Analogues", filed Dec. 11, 2017, which is incorporated herein by reference in its entirety.

FIELD OF THE INVENTION

This invention is directed to the field of threat substances detection, and in particular, to the field of detection of illegal drugs.

BACKGROUND OF THE INVENTION

Fentanyl and its analogues are opioids whose abuse has spawned major crises in Canada and the US. Low exposure levels of 1-2 mg are lethal and were the cause of over 60,000 overdose cases in the US and approximately 6,000 cases in Canada in 2016. First responders and their canines are coming into contact with these drugs which contact occasionally results in intoxication and the need for emergency medical treatment. Present analytical systems require sample collection and testing in a laboratory, which takes time to produce results. These are not field deployable technologies.

The epidemic of opioid overdose cases in the US and Canada from opioids has reached alarming levels. These drugs are inhaled, may lead to respiratory arrest and are 50 times more lethal than heroin and 100 times more lethal than morphine.

Several technologies are in the market and consist of desk top or hand held ion mobility detectors, portable infrared chemical identifiers and laser Raman handheld detectors. These technologies allow users to test bulk quantities of unknown substances, provided they are programmed in their libraries and are accessible to the user. The drawbacks of these techniques are cost, limited ability to detect traces of airborne drugs or vapors, and the requirement that all fentanyl analogues be programmed into their libraries. There are over 40 Fentanyl analogues in circulation and not all are commercially available for standard programming of detectors. Also, real street drugs are usually mixed and adulterated with other drugs or acting agents that might interfere with the detection of the opioids. The limitations of these devices in day-to-day operation of first responders and police officers put them at risk and threaten their safety during a response.

SUMMARY

The innovation involves a (preferably) wearable drugs detector that preferably provides specific signals for, for example, Fentanyl and its analogues, and alerts the user of unacceptably high (e.g. lethal) levels of the drugs in the air. The preferred embodiment of the device is small, and battery operated, with an internal micro-pump to draw the air through a heated ionizing surface inducing positive and negative ions fragments of the drug. These ions under a potential are made to migrate to opposite polarity collectors. The induced signals at the collectors are filtered and amplified at their respective high sensitivity electrometers. The signals are processed through a programmed CPU, reporting audible and visual alarms if, for example, Fentanyl based molecules are encountered.

Therefore, according to an aspect of the invention, there is provided wearable device for sensing airborne narcotics, comprising an air intake; an ionization apparatus for ionization of molecules of airborne narcotics, the apparatus comprising a heated surface in fluid communication with the intake for heating molecules of airborne narcotics to ionize said molecules; at least one collector for receiving ions resulting from said ionization, and generating a signal; an apparatus for creating electrical potential to draw said ions to said at least one collector; an alarm generator for generating an alarm if a time gap between said creation of ions and said signal indicates a presence of an airborne narcotic. Optionally, the heated surface comprises a filament. Optionally, the air intake includes a micropump. Optionally, the alarm generator includes a microprocessor.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
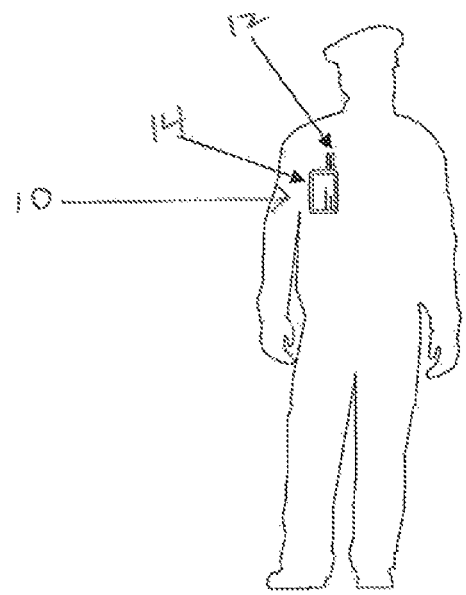
FIG. 1 is a conceptual drawing of a wearable Fentanyl detector close to breathing area of a person.

While embodiments of the disclosure are amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION OF THE INVENTION

Figure 2:
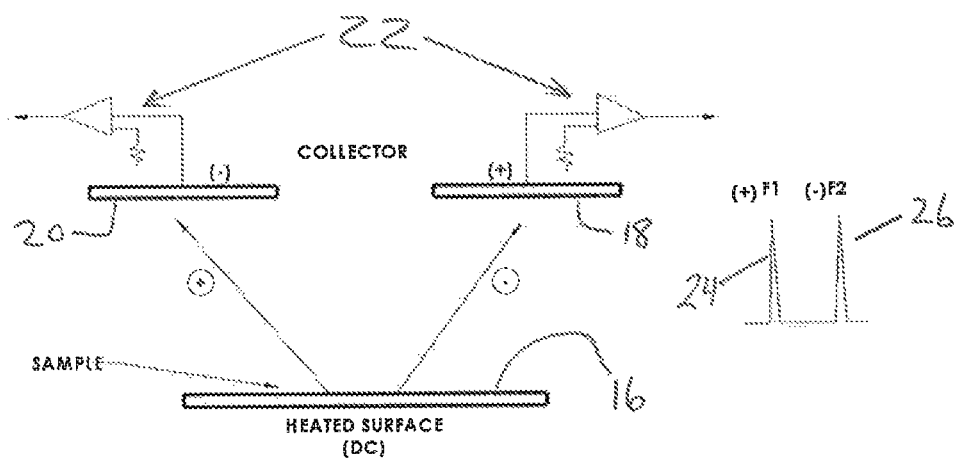
FIG. 2 is a schematic representation of a process of sample fragmentation, ionization and detection.

FIG. 1 shows a person wearing a wearable detector 10, comprising an intake 12, and sensor portion 14. FIG. 2 shows a heated surface 16. Ions are drawn to positive collector plate 18 or negative collector plate 20. In this embodiment, the collector plates are connected to an amplifiers/filters 22 for the signals generated by the collectors. Also shown in FIG. 2 are example signals 26 and 24 generated by the collectors.

In the preferred embodiment, the basic operation of the detector involves selective ionization of fragmented drug molecules on a heated surface. Examples of surfaces include platinum wire, Tungsten, and platinum/Rhodium wire that normally has relatively high work function. The opioids molecule is sampled directly over the heated surface to undergo selective fragmentation and ionization into positive and negative ions as shown in equation 1.

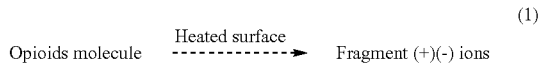

(1)

In the preferred embodiment, the ionization current for the positive and negative ions is determined by the efficiency of the formation of the fragment ions on the heated surface and also by the ionization efficiency of the process. This can be presented by equation 2.

$$\text{Efficiency} = (N_\pm/N_o) = \alpha e^{(W-IE)/KT} \quad (2)$$

Where $N_\pm$ is the number of positive and negative ions leaving the surface per unit area,
$N_o$ is the number of neutral molecules hitting the surface,
W is the work function of the surface,
KT is Boltzmann constant and temperature of the surface,
IE is the ionization energy of the emitted fragments, and
$\alpha$ is statical ratio of ions and neutral species.

Organic molecules undergo decomposition which have lower ionization energies and produce specific ionized species, which can be used to identify the parent molecule.

In the preferred embodiment, a potential is applied to the ions to direct each ionized species to a polarized collector plate for registering a signal for both positive and negative ion species generated from the heated surface.

As indicated by Equation 2, the surface preferably has good pyrolytic properties with high work function in order to produce sufficient amounts of ionized species of the impacted neutral drug molecules. Another factor that will influence the ionic yield is the temperature of the surface. Preferably, that temperature is set in the range of 500-800° C.

FIG. 2 shows the process of fragmentation and ionization followed by detection of opioids molecules entering the sensor heated surface.

Fentanyl and its analogues have demonstrated a specific fragmentation pass during thermal heating and ionization using a radioactive source nickel-63 of 15 mCi strength. This effect was observed in a gas chromatograph interfaced to an ion mobility spectrometer with fast polarity switching capability.

Table 1 lists Fentanyl and seven analogues with GC retention times in seconds and corresponding positive and negative ions reduced mobility constants. The produced fragments are basically within experimental errors are similar as well as the observed ions reduced mobility constant. This similar behavior of Fentanyl and its analogues in producing similar if not identical fragmentation and ionization species is the basis of the innovation presented herein.

The basis of the fragmentation process is loss of various functional groups of the molecule. For example, Fentanyl loses a toluene group of the molecule. Similarly, other functional groups are lost, like acetyl or five member ring sulfur group to produce similar fragment molecules which are ionized in both polarities. These fragment ions have similar chromatography, ion mass and drift times that would permit the use of a universal and simple sensor for the large number of Fentanyl analogues.

TABLE 1

Specific Fragmentation & Ionization of Fentanyl and seven Analogues

Figure 3:
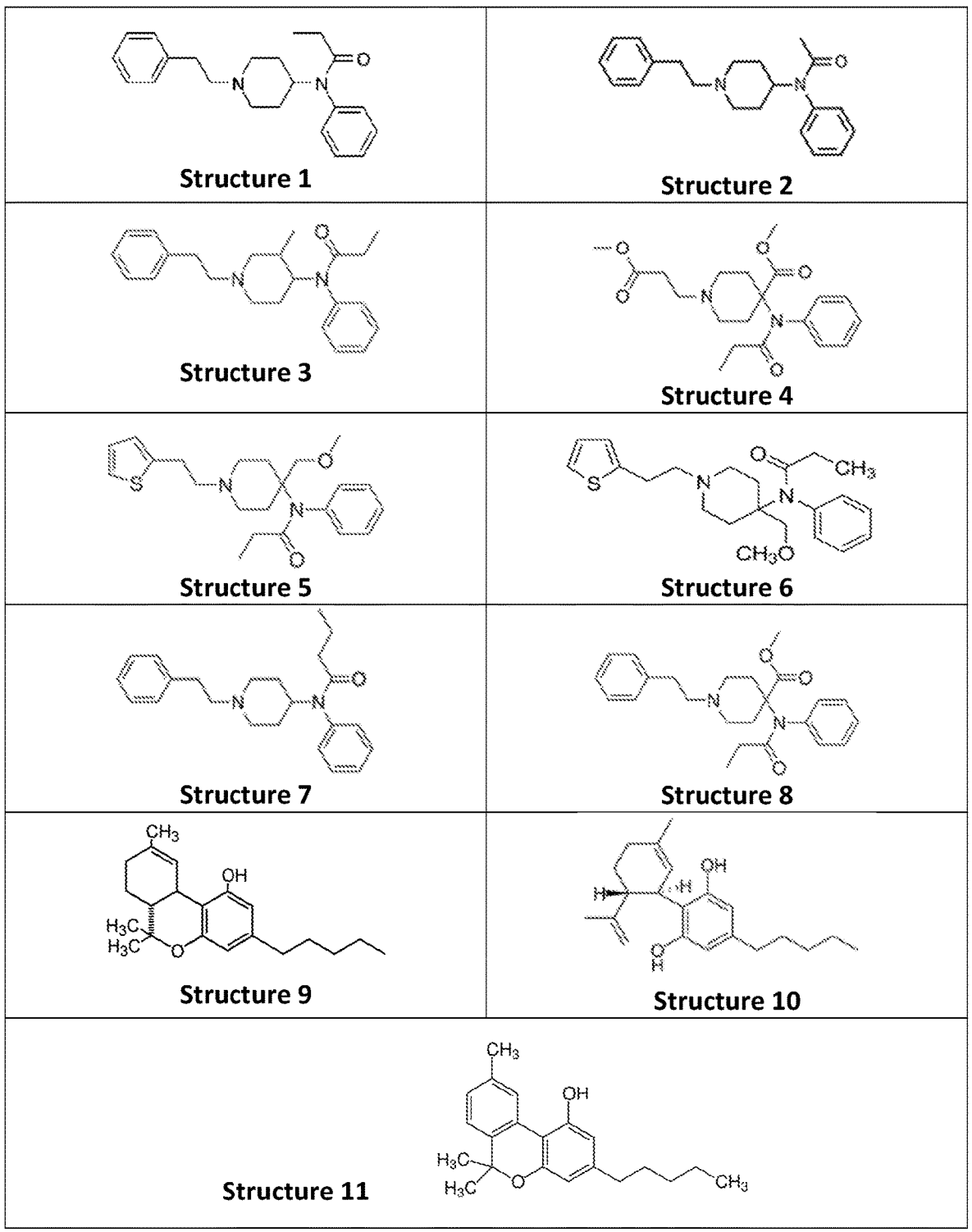
FIG. 3 is a table showing the molecular structures of Tables 1 and 2.

| Name | M.W | Molecular Formula | Mode | Retention Time(sec) | Drift Time | Mobility constant | Molecular Structure (as shown in FIG. 3) |
|---|---|---|---|---|---|---|---|
| Fentanyl | 336.47 | $C_{22}H_{28}N_2O$ | (+) | 35 | 10.15 | 1.536 | Structure 1 |
|  |  |  | (−) | 35 | 10.39 | 1.512 |  |
| Acetyl Fentanyl | 322.44 | $C_{21}H_{26}N_2O$ | (+) | 35 | 10.17 | 1.539 | Structure 2 |
|  |  |  | (−) | 35 | 10.41 | 1.512 |  |
| 3-Methyl Fentanyl | 350.50 | $C_{23}H_{30}N_2O$ | (+) | 35 | 10.21 | 1.538 | Structure 3 |
|  |  |  | (−) | 35 | 10.45 | 1.511 |  |
| Remifentanil | 376.45 | $C_{20}H_{28}N_2O_5$ | (+) | 35 | 10.45 | 1.511 | Structure 4 |
|  |  |  | (−) | 35 | 10.45 | 1.511 |  |
| Sufentanil | 386.55 | $C_{22}H_{30}N_2O_2S$ | (+) | 35 | 10.19 | 1.535 | Structure 5 |
|  |  |  | (−) | 35 | 10.41 | 1.512 |  |
| Alfentanil | 416.52 | $C_{21}H_{32}N_6O_3$ | (+) | 35 | 10.17 | 1.538 | Structure 6 |
|  |  |  | (−) | 35 | 10.41 | 1.511 |  |
| Butyryl Fentanyl | 350.50 | $C_{23}H_{30}N_2O$ | (+) | 35 | 10.21 | 1.536 | Structure 7 |
|  |  |  | (−) | 35 | 10.45 | 1.512 |  |
| Carfentanil | 394.51 | $C_{24}H_{30}N_2O_3$ | (+) | 35 | 10.21 | 1.537 | Structure 8 |
|  |  |  | (−) | 35 | 10.45 | 1.510 |  |

Drift time is in milliseconds, reduced mobility constant has units of $cm^2/V \cdot sec$, and GC retention time is in seconds. Molecular weight is in gram/mole.

In a further embodiment, the process described in FIG. 2 can also be configured to determine key marijuana components such as Tetrahydrocannabinol (THC), Cannabidiol (CBD) and Cannabinol (CBN).

Table 2 list the observed chromatography peaks (GC), drift times in millisecond and reduced mobility constants in both positive and negative ion polarity.

TABLE 2

Marijuana Key components

| Marijuana | MW | Formula | Mode | Retention time | Drift time | $K_o$ | Molecular Structure (as shown in FIG. 3) |
|---|---|---|---|---|---|---|---|
| THC | 314.5 | $C_{21}H_{30}O_2$ | (+) | 110 | 7.47 | 1.058 | Structure 9 |
|  |  |  | (−) |  | 8.15 | 0.985 |  |
| CBD | 314.5 | $C_{21}H_{30}O_2$ | (+) | 98 | 7.52 | 1.060 | Structure 10 |
|  |  |  | (−) |  | 8.10 | 0.997 |  |
| CBN | 310.4 | $C_{21}H_{26}O_2$ | (+) | 110 | 7.48 | 1.067 | Structure 11 |
|  |  |  | (−) |  | 8.15 | 0.992 |  |

The marijuana components produced similar ionic species which are detectable in both positive and mode ion detection scheme. The response of the sensor to both positive and negative ions at their respective drift time or reduced mobility constants will constitute an alert associated with the target analyte.

The alarm logic associated with the ions migration to the collectors can be configured to trigger an alarm in the event that the detected species are in accordance to drift timing or relative to an internal standard in converting drift time to reduced mobility constants at constant temperature and pressure. In other words, the drift time, mobility constants and other data are known, or can be determined, for various drugs, opioids and marijuana, as illustrated above. The time that passes between commencement of ionization, and a signal on a collector, can be therefore used to determine if the relevant substance has been detected. If yes, an alarm is triggered.

Other embodiments of the invention will be apparent to those skilled in the art from consideration of the specification and practice of the embodiment disclosed herein. Although one or more methods have been described in conjunction with the wearable Fentanyl and its analogues sensor, the invention can apply to other hard and soft drugs like cocaine, heroin, ketamine, amphetamine, methamphetamine, PCP and other street drugs.

The above references to U.S. patents and patent publications in all sections of this application are herein incorporated by references in their entirety for all purposes. Components illustrated in such patents may be utilized with embodiments herein.

All of the features disclosed in this specification (including the references incorporated by reference, including any accompanying claims, abstract and drawings), and/or all of the steps of any method or process so disclosed, may be combined in any combination, except combinations where at least some of such features and/or steps are mutually exclusive.

Each feature disclosed in this specification (including references incorporated by reference, any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any incorporated by reference references, any accompanying claims, abstract and drawings), or to any novel one, or any novel combination, of the steps of any method or process so disclosed. The above references in all sections of this application are herein incorporated by references in their entirety for all purposes.

Although specific examples have been illustrated and described herein, it will be appreciated by those of ordinary skill in the art that any arrangement calculated to achieve the same purpose could be substituted for the specific examples shown. This application is intended to cover adaptations or variations of the present subject matter. Therefore, it is intended that the invention be defined by the attached claims and their legal equivalents, as well as the following illustrative aspects. The above described aspects embodiments of the invention are merely descriptive of its principles and are not to be considered limiting. Further modifications of the invention herein disclosed will occur to those skilled in the respective arts and all such modifications are deemed to be within the scope of the invention.

The invention claimed is:

1. A wearable device for sensing airborne narcotics, comprising:
   an air intake;
   an ionization apparatus for ionization of molecules of airborne narcotics, the apparatus comprising a heated surface in fluid communication with the intake for heating molecules of airborne narcotics to ionize said molecules;
   at least one collector for receiving ions resulting from said ionization, and generating a signal;
   an apparatus for creating electrical potential to draw said ions to said at least one collector; and
   an alarm generator for generating an alarm if a time gap between said creation of ions and said signal indicates a presence of an airborne narcotic.

2. A wearable device as claimed in claim 1, wherein the heated surface comprises a filament.

3. A wearable device as claimed in claim 1, wherein the air intake includes a micropump.

4. A wearable device as claimed in claim 1, wherein the alarm generator includes a microprocessor.

* * * * *